(12) United States Patent
Vilsmeier et al.

(10) Patent No.: US 7,862,568 B2
(45) Date of Patent: Jan. 4, 2011

(54) FIXING DEVICE

(75) Inventors: Stefan Vilsmeier, Munchen (AT);
Rainer Birkenbach, Aufkirchen (DE);
Eric Merlin, Feldkirchen (DE)

(73) Assignee: BrainLAB AG, Feldkirchen (DE)

( * ) Notice: Subject to any disclaimer, the term of this patent is extended or adjusted under 35 U.S.C. 154(b) by 166 days.

(21) Appl. No.: 11/681,385

(22) Filed: Mar. 2, 2007

(65) Prior Publication Data
US 2007/0160439 A1    Jul. 12, 2007

Related U.S. Application Data

(63) Continuation of application No. 10/001,952, filed on Oct. 31, 2001, now abandoned.

(51) Int. Cl.
*A61F 2/46* (2006.01)
(52) U.S. Cl. .................................................. 606/86 R
(58) Field of Classification Search ................... 606/53, 606/62, 65–67, 72–73, 130, 300–302, 304–305, 606/309–314, 318, 319–320, 54, 102; 411/378, 411/418, 315, 321; 600/429
See application file for complete search history.

(56) References Cited

U.S. PATENT DOCUMENTS

| | | | | |
|---|---|---|---|---|
| 159,306 A * | 2/1875 | Cummings | .................. | 411/321 |
| 216,222 A * | 6/1879 | Schifferly | .................. | 411/321 |
| 1,000,280 A * | 8/1911 | Messenger | .................. | 411/418 |
| 1,201,864 A * | 10/1916 | Overmeyer | .................. | 606/54 |
| 1,495,687 A * | 5/1924 | Grosclaude | .................. | 470/2 |
| 1,829,293 A * | 10/1931 | Olson | .................. | 411/140 |
| 1,909,476 A * | 5/1933 | Trotter | .................. | 411/386 |
| 2,143,922 A * | 1/1939 | Longfellow | .................. | 606/60 |
| 2,367,399 A * | 1/1945 | Isakson | .................. | 411/277 |
| 2,400,348 A * | 5/1946 | Greene | .................. | 411/107 |
| 4,754,749 A | 7/1988 | Tsou | | |
| 5,662,651 A | 9/1997 | Tornier et al. | | |
| 5,733,289 A * | 3/1998 | Seedhom et al. | .................. | 606/80 |
| 6,021,343 A * | 2/2000 | Foley et al. | .................. | 600/429 |
| 6,033,407 A * | 3/2000 | Behrens | .................. | 606/62 |
| 6,048,151 A | 4/2000 | Kwee | | |
| 6,183,474 B1 | 2/2001 | Bramlet et al. | | |
| 6,203,543 B1 * | 3/2001 | Glossop | .................. | 606/60 |
| 6,711,431 B2 | 3/2004 | Sarin et al. | | |
| 6,719,757 B2 | 4/2004 | Neubauer et al. | | |
| 6,856,828 B2 * | 2/2005 | Cossette et al. | .................. | 600/429 |
| 2002/0107518 A1 * | 8/2002 | Neubauer et al. | .................. | 606/54 |

FOREIGN PATENT DOCUMENTS

DE    20103416 U1 *  7/2001
WO    00/66045      11/2000

* cited by examiner

*Primary Examiner*—Thomas C Barrett
*Assistant Examiner*—Nicholas Woodall
(74) *Attorney, Agent, or Firm*—Renner, Otto, Boisselle & Sklar, LLP

(57) ABSTRACT

The present invention relates to a fixing device comprising at least one guide for a securing element, a fixing system comprising such a fixing device and at least one securing element, as well as a positioning system comprising such a fixing system, and a positioning element.

19 Claims, 4 Drawing Sheets

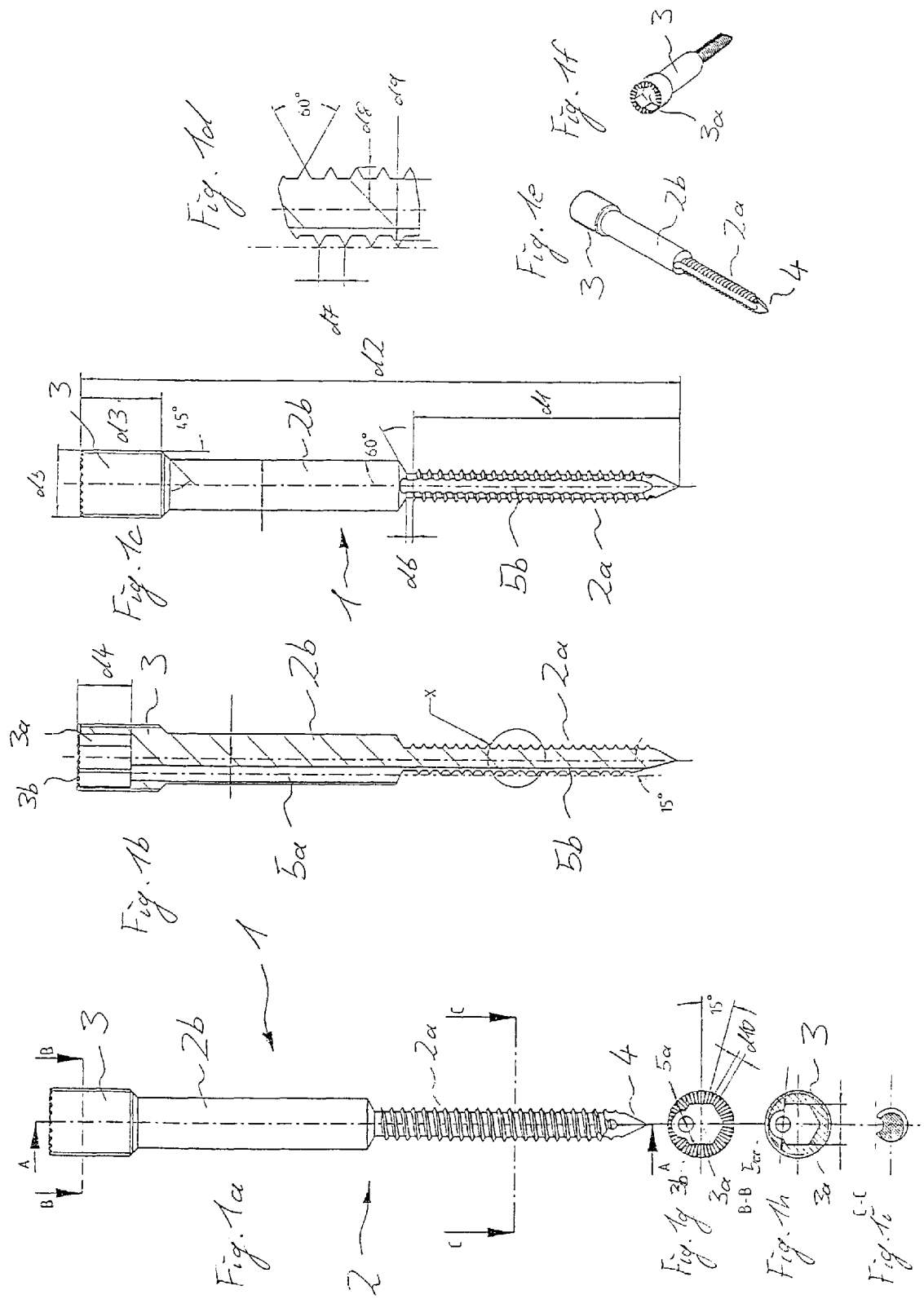

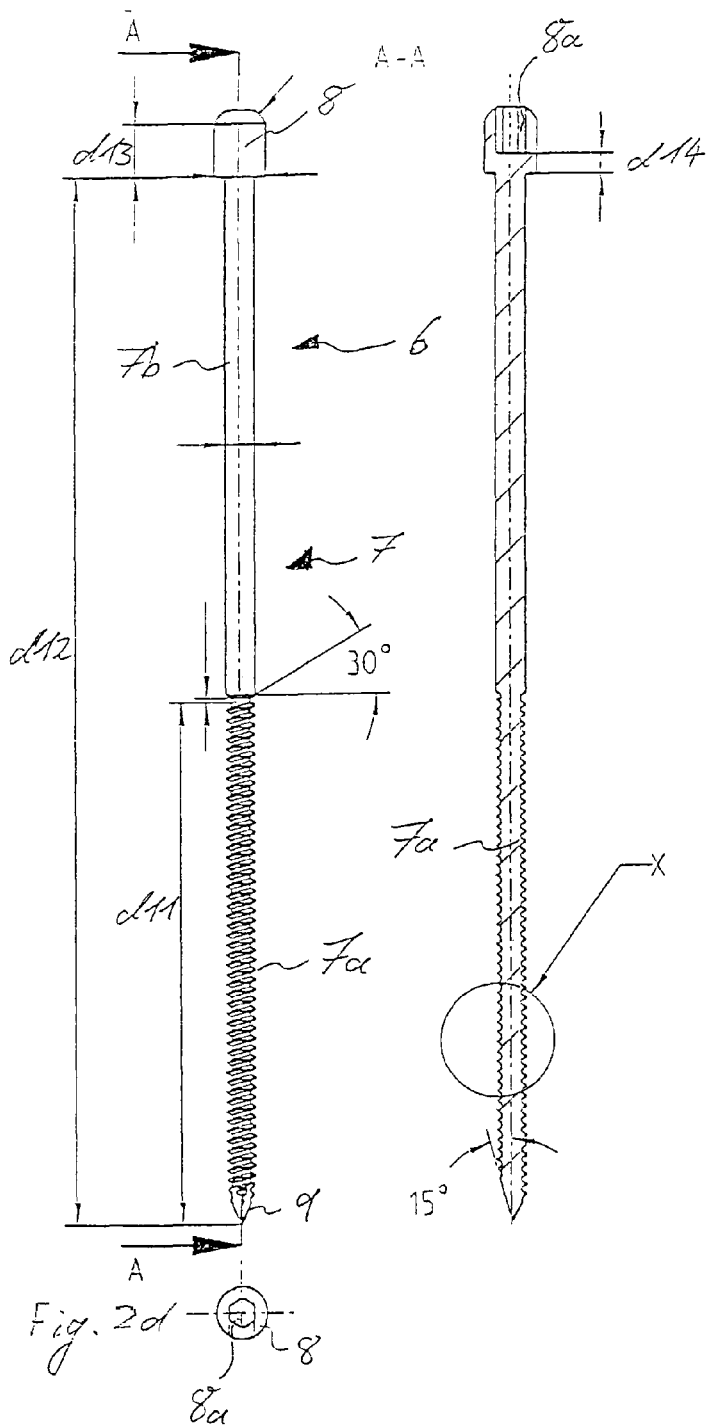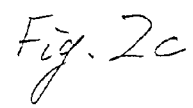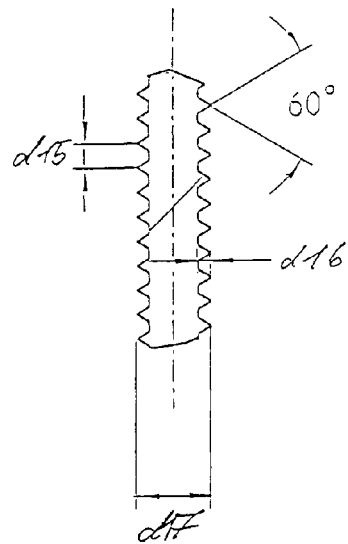

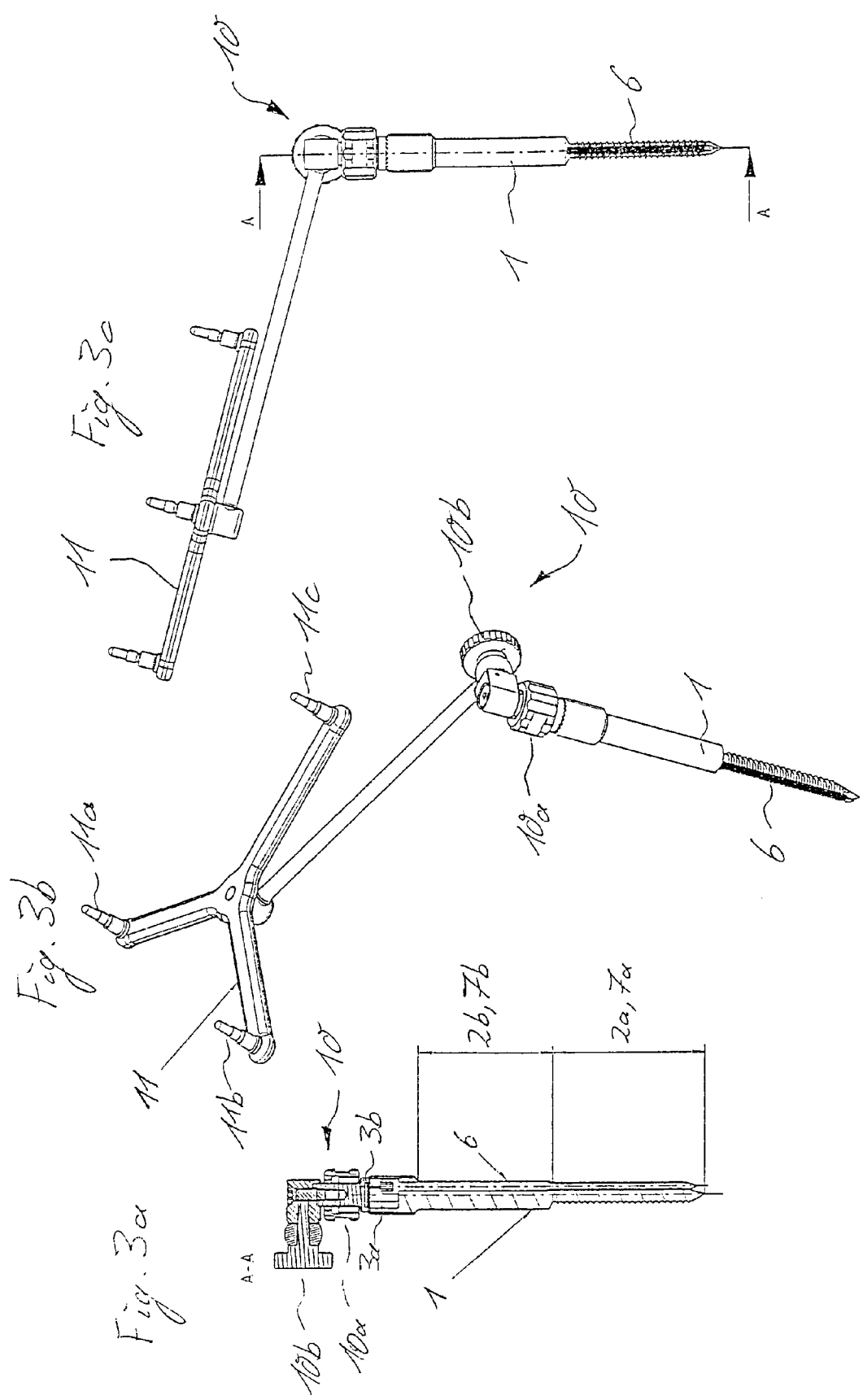

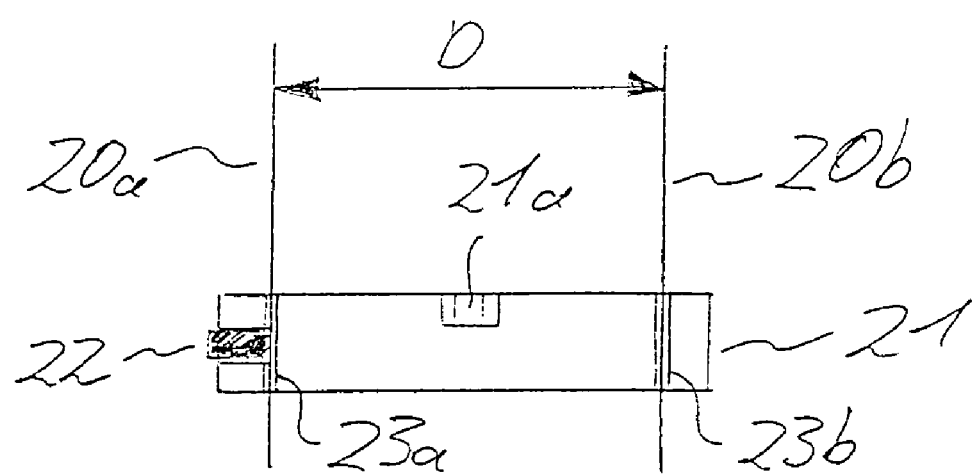

FIXING DEVICE

RELATED APPLICATION DATA

This application is a continuation of application Ser. No. 10/001,952 filed on Oct. 31, 2001, which is hereby incorporated herein by reference.

FIELD OF THE INVENTION

The present invention relates to a fixing device and a fixing system, in particular for attaching a positioning element, (e.q., a marker) in a firmly defined positional relationship to an object (e.q., a bone).

BACKGROUND OF THE INVENTION

In surgery, for example a knee or hip operation, in particular when attaching an implant, it is necessary in modern surgical techniques to determine as accurately as possible the precise spatial position of a specified body structure, e.g. the position of the femur and tibia, in order to be able to carry out the most precise surgery possible using suitable navigational instruments. In this way, for example, an artificial knee joint can be positioned exactly on the femur and tibia using images made pre-operatively or intra-operatively and suitable calculations, such that the optimum location is guaranteed. In general, for determining the position of a bone structure, a screw is screwed into the bone, and a marker is attached to said screw. From the position of the marker recorded by a camera, conclusions can be drawn as to the position of the bone. If there are any slight shifts between the bone and the maker attached to it by means of the screw, e.g. due to a slight turning of the screw, then an incorrect position of the bone is concluded from the recorded position of the marker, which can have a considerable effect on the success of the operation. Deviations in the range of one to two degrees, for example, can lead to clearly noticeable incorrect positioning of an implanted knee joint, which can become noticeable through problems in the knee joint's ability to function and in a substantially shortened life-span, since the knee joint can no longer optimally take the strain due to the slightly incorrect positioning.

In particular in the case of screws typically used, the problem occurs that a screw inserted into a bone is unintentionally turned slightly, such that surgery is not performed precisely.

It is an object of the present invention to propose a fixing device and a fixing system which facilitate the precise and secure positioning of at least one marker on an object, such as for example a bone.

This object is solved by a fixing device and a fixing system comprising the features of the independent claims. Advantageous embodiments are given by the sub-claims.

SUMMARY OF THE INVENTION

Although the technical field of the invention was described in the context of surgery in the area of the knee, the invention can be applied in a broad range of surgery or of technical systems in general, for example in surgery in the area of the hip, the spinal column or the head. In general, the invention can be used anywhere where it is necessary to attach a specific element, such as for example a marker, to an object, for example to a bone or a bone structure, in a way which is as stable as possible and secure against turning or shifting.

The fixing device in accordance with the invention comprises at least one guide for a securing element. By means of this guide, a securing element can be inserted into the bone before, during or after the insertion of the fixing device into, for example, a bone, in order to secure the inserted fixing device against undesired movement, such as for example a slight turning, by inserting the securing element further.

The fixing element is advantageously constructed in a long and approximately cylindrical form and preferably comprises a shaft, wherein a part of the shaft is preferably suitable for being inserted into a bone. At an end of the shaft which is not to be inserted into a bone, a head is preferably provided which can be suitably formed in order, for example, to position a tool for inserting the fixing device and/or for fixing at least one positioning element as securely as possible to it.

The shaft advantageously comprises an operative section at an outer end and an intermediate section, which is arranged between the operative section and the head of the fixing device. The operative section is preferably formed in such a way that inserting the fixing device into an object, such as for example a bone, is enabled, wherein it should also be ensured by the operative section, after insertion, that e.g. the marker is fixed as stable as possible.

The diameter of the intermediate section is advantageously larger than the diameter of the operative section, although both sections may also be formed with approximately the same diameter, or the operative section also exhibit a smaller diameter than the intermediate section. The transition between the operative section and the intermediate section is advantageously formed conically, in order to avoid a sharp transition between the operative section and the intermediate section. If, for example, the operative section has a smaller diameter than the intermediate section, the fixing device can for example be inserted into an object up until further insertion of the fixing device is prevented or made difficult by the larger diameter of the intermediate section.

The guide in accordance with the invention is advantageously formed as a bore and/or as a recess. Preferably, the guide can also consist, as a combination, of a bore or a through-hole of a head or shaft section, wherein other shaft sections can include a recess or a further bore or even no guide. The guide is advantageously formed such that it runs approximately in the longitudinal direction of the fixing device, preferably parallel to it, and advantageously with a small side offsetting of e.g. 0.1 to 10 mm to the middle axis of the operative section. It is generally advantageous if the fixing device comprises at least one bore through which a securing element can be inserted and held in place, wherein a semicircular or circular recess is advantageously provided in the operative section, in order to guide the securing element along the operative section, if for example the bore is arranged in the intermediate section of the shaft and the distance between the middle axis of the bore and the middle axis of the operative section is smaller than the diameter of the operative section. In accordance with the invention, the guide for the securing element can be formed in such as way that the outer circumference of the guide and/or of an inserted securing element overlaps with the outer circumference of the operative section, such that the securing element is preferably guided along the operative section and inserted near or adjacent to the operative section. Alternatively, the guide can also be formed in such a way that a securing element to be inserted and the shaft or operative section of the fixing device do not lie directly adjacent to each other, but exhibit a distance from each other, for example in the range 0.1 to 10 mm, wherein the securing element is guided, for example, through a bore of the head or of a shaft section.

Advantageously, more than one guide, for example 2, 3, 4 or up to 10 or more guides, can be provided on the fixing device in order to be able to insert a number of securing elements. In this case, the guides can be formed parallel to one another and to a middle axis of the operative section. It is also possible to arrange the guides in such a way that the securing elements can be inserted into the fixing device at a specified angle to each other, and as appropriate also to a middle axis of the operative section, in order for example to fix or secure the fixing device more firmly.

In accordance with a preferred embodiment, the fixing device in accordance with the invention is formed as a screw and comprises a thread in the operative section, wherein a guide hole can be provided in the operative section going right through the thread. As an alternative to or in addition to a guide hole for a securing element, a side recess can be provided in the operative section, such that the screwing process is interrupted in one or more places in order to be able to insert one or more securing elements along the operative section.

The operative section can also be formed as a nail, wherein similarly at least one guide can be provided in the operative section. In this case, the external area of the operative section can be essentially even, wherein for example one or more edges can be provided along the length of the direction of insertion, in order to facilitate inserting the fixing device and to impede or prevent subsequent undesired turning.

A tapered section id advantageously formed at the outer end of the insertion area, for example in the form of a small cone or a pyramid with one or more side edges, in order to facilitate placing and inserting the fixing device.

A connection element, for example a jutting part or an indented part, for example a plug-in opening, is preferably provided in the area of or on the head of the fixing device, in order for example to be able to position a tool for inserting the fixing device and/or to be able to connect a positioning element or other desired objects to the fixing device as secure against twisting as possible. To this end, a jutting part and/or a plug-in opening is preferably formed not rotationally symmetric, and can comprise one or more edges, such that for example an Allen key can be inserted into the head of the fixing device in order to screw it into a bone, and then a positioning element rotationally secure with respect to the fixing device, such as for example a reference star, can be fixed onto it, once a securing element has been inserted. A number of indented parts can also advantageously be provided on the head in order to be able to attach a positioning element to be attached, rotationally secure, onto the fixing device in a number of different angle positions.

In accordance with a further aspect of the invention, a fixing system is proposed which consists of the fixing device described above, wherein at least one securing element is inserted into the at least one guide of the fixing device. The securing element can be formed for example as a screw and advantageously exhibits a long cylindrical shape, wherein the outer diameter of the securing element is preferably formed in such a way that the securing element can be guided through the guide of the fixing element with only little or no play. The securing element can also comprise a head and a shaft, just like the fixing device described above, which for example is in turn subdivided into an operative section and an intermediate section. With respect to possible arrangements of the shaft and/or head, reference is made to the features described above for the fixing device, which can also be formed in the securing element.

The diameter of the securing element is preferably smaller than the diameter of the fixing device, in particular smaller than the diameter of its operative section.

In accordance with a further aspect of the invention, a positioning system is proposed which consists of the fixing system as described above and which further comprises a positioning element fixed thereto, such as for example at least one marker or a reference star with three markers and/or holding devices for the corresponding markers.

The positioning system is advantageously formed in such a way that the positioning element attached to the fixing system can be adjusted, for example rotated about at least one axis, such that the best possible alignment of the positioning element can be set. In so doing, the positioning element can preferably be arrested in the set position, so that any unintentional tilting or pivoting of the positioning element relative to the fixing system can be substantially prevented.

BRIEF DESCRIPTION OF THE DRAWINGS

The invention will now be described by way of a preferred example embodiment. The figures show:

FIGS. 1a to 1i an embodiment in accordance with the invention of a fixing element comprising a guide;

FIGS. 2a to 2d an embodiment of a securing element which can be inserted into the fixing device in FIG. 1;

FIGS. 3a to 3c a positioning system in accordance with the invention; and

FIG. 4 an alternative embodiment of a fixing device in accordance with the invention.

DETAILED DESCRIPTION

FIG. 1a shows, in a horizontal projection, a fixing device 1 composed of a shaft 2 and a head 3. The shaft 2 comprises an operative section 2a formed as a screw and an intermediate section 2b having a larger outer diameter than the operative section 2a. The transition sections between the operative section 2a, the intermediate section 2b and the head 3 are conically formed as cone sections, such that the respective sections carry on from one other without sharp edges. A tip 4 is formed at the lower end of the operative section 2a which has a number of side edges, as can be seen in FIG. 1e. The tip 4 makes it easier to position and insert the fixing device 1.

FIG. 1b shows a cross-section of the fixing device shown in FIG. 1 along the line A-A. The bore 5a, which serves as the guide for a securing element, can be seen in the intermediate section 2b and the head 3, wherein the guide—as indicated by the dot-dash line—is formed as a groove or recess 5b outside the through-hole 5a in the areas of the operative section 2a, such that a securing element can be guided through the head 3 and the intermediate section 2b along the operative section 2a, and thus for example can also, after the fixing device has been inserted into, for example, a bone, likewise be inserted into the bone approximately parallel to the direction of penetration of the fixing device through the guide 5a, 5b, in order to make the fixing device rotationally secure.

The head 3 comprises a recess 3a, as can also be seen in the perspective view in FIG. 1f and the horizontal projection in FIG. 1g, which in cross-section forms an approximately uniform hexagon, in order for example to be able to position an Allen key or an attachable element. The recess 3a is formed semicircular on one side in order to enable the insertion of a securing element into the guide hole 5a, as shown in FIG. 3a.

FIG. 1c shows the fixing device 1 shown in FIG. 1a, rotated through 180°. The groove or guide recess 5b running along the operative section 2a can be seen, which interrupts the thread of the screw such that a securing element can be guided parallel to the screw.

In accordance with a preferred embodiment of the fixing device, example dimensions for the fixing device in accordance with the invention may be as follows: Length d1 of the operative section 2a=40 mm; total length d2 of the fixing device 1=90 mm; length d3 of the head 3=12 mm; depth d4 of the recess 3a in the head 3=8 mm; and diameter d5 of the head 3=10 mm. An edge of the tip 4 is formed, for example, inclined at 15° to the longitudinal axis of the fixing device. The transition area between the operative section 2a and the intermediate section 2b comprises a small distance area of length d6=1 mm, to which a small cone-shaped connecting piece is connected with an angle of the shell surface of the cone stump of 60° with respect to the longitudinal axis. FIG. 1d shows section X, identified in FIG. 1b, of the operative section 2a provided with a thread. In the embodiment shown, the lead d7 of the thread=1.6 mm, wherein the thread projects out by d8=0.7 mm. The distance d9 from a turn of the thread to an internal section of the screw in the cut plane is 3.6 mm.

FIG. 1g shows a horizontal projection of the fixing device 1, wherein a number of recesses 3b running around the head can be seen. In the embodiment shown, two small recesses or grooves 3b are arranged within a distance d10=1 mm, running around the upper part of the head 3. These circumferential recesses 3b enable a reference star, for example, to be attached rotationally secure in a number of turning positions, wherein the reference star can be attached and/or arrested rotationally secure on the fixing device, in various angle positions relative to head 3 through the recesses 3b.

FIG. 1h shows a cross-section view along the line B-B of the fixing device shown in FIG. 1a. As can also be seen in FIG. 1g, the external circumference of the recess 3a is formed in such a way that on the one side a securing element can be inserted through the through-hole 5a serving as a guide, and then once the securing element has been inserted through the recess 3a which comprises several edges, an attachment can be attached rotationally securely to the fixing device 1.

FIG. 1i shows a cross-section along the line C-C of the operative section 2a shown in FIG. 1.

The actual dimensions specified above for the embodiment, shown in FIG. 1, of a fixing device 1 in accordance with the invention are only to be regarded as examples for describing the invention and are intended to make it clear that the fixing device in accordance with the invention enables, for example, a reference star to be securely positioned to a bone by means of extremely slight surgery.

FIGS. 2a to 2d show an example embodiment of a securing element 6 which can be used together with the fixing device 1 in accordance with the invention illustrated in FIG. 1. The securing element 6 comprises a shaft 7 and a head 8. The shaft 7 is subdivided into an operative section 7a provided with a screw thread, to which a tip 9 is provided at the lower end and which lies adjacent to the intermediate section 7b at the end opposite the tip 9, said intermediate section lying between the operative section 7a and the head 8. The head 8 further comprises a recess 8a which is formed in the shape of a hexagon, as shown in the horizontal projection in FIG. 2d, in order for example to position an Allan key on the head 8 of the securing element 6, to screw the securing element 6 in through the guide 5 of the fixing device 1 screwed into for example a bone, and in this way to prevent the fixing device 1 from turning, as illustrated for example in the cross-sectional view in FIG. 3a. In the embodiment shown, the fixing device 1 is generally made rotationally secure by the fact that, once the securing element 6 has been inserted into the fixing device 1, the operative sections 2a and 7a lying adjacent to each other no longer represent a rotationally symmetrical form, such that the fixing device 1 is prevented from turning by the securing element 6. Possible turning by the securing element 6 does not, however, effect the position of the fixing device 1.

Example dimensions of the securing element 6 shown in FIG. 2 are: Length d11 of the operative section 7a=40 mm; length d12 of the shaft 7=80 mm; length d13 of the head 8=4 mm; and length d14 of the head 8 in which no recess 8a is provided=1.5 mm.

The measurements given are only to be regarded as example embodiments and are intended to make it clear that, using the device in accordance with the invention, only relatively minor surgery is necessary. It is possible for the fixing device 1 and the securing element 6 to exhibit approximately the same length, and to exhibit approximately similar dimensions with respect to the operative sections 2a, 7a and the intermediate sections 2b and 7b. A longer or shorter securing element, with a longer or shorter operative section 7a and/or intermediate section 7b, can however also be used. In general, it is advantageous if the securing element is formed in such a way that the total length including the head 8 is smaller than the total length of the fixing device 1, such that if the securing element 6 no longer projects out of the head 3, or is in particular completely inserted into the fixing device 1, i.e. the tips 4 and 9 lie approximately next to each other, the head 8 of the securing element 6 can be countersunk in the lower part of the head 3 of the fixing device 1, such that the complete recess 3a of the head 3 can be used for inserting, for example, a reference star, without the head 8 of the inserted securing element 6 projecting into the recess 3a.

FIG. 2c shows an enlargement of the operative section 7a designated X in FIG. 2b. The lead d15 of the thread is 0.75 mm in the embodiment shown; the thread projects out of the outer surface of the operative section 7a by d16=0.4 mm, and the outer diameter of the thread is d17=2.3 mm.

FIGS. 3a to 3d show a positioning system in accordance with the invention, wherein the securing element 6 shown in FIG. 2 is inserted into the fixing device shown in FIG. 1.

FIG. 3c shows a horizontal projection of a positioning system, wherein a reference star 11 serving as a positioning element is positioned on the fixing system 1, 6; markers can be attached to the holding devices 11a, 11b and 11c of the reference star, respectively. The reference star 11 is fixed to the fixing system 1,6 by means of an adjustable aligning device 10.

FIG. 3b shows the positioning system illustrated in FIG. 3c in a perspective view. The aligning device 10 comprises a screw 10a which can be used for fixing to the fixing system 1, 6 and/or for turning the reference star 11 fixed to it about the longitudinal axis of the fixing device 1. Via a further screw 10b, the reference star 11 can be turned around an axis which is approximately perpendicular to the middle axis of the fixing device 1. By using the aligning device 10, the reference star 11 can be attached to a fixing system 1, 6 inserted for example into a bone, and can be positioned for good detection of the markers (not shown) attached to the reference star 11.

FIG. 3a shows a cross-section along the line A-A of the positioning system shown in FIG. 3c. Here, it can be seen that when the securing element 6 is inserted in the fixing device 1, the operative sections 2a, 7a and the intermediate sections 2b, 7b are approximately adjacent to each other. The aligning device 10 is inserted into the recess 3a of the fixing device and fixed to it. Through projections and/or recesses on the underside of the aligning device 10, which engage with the projections or recesses 3b on the top side of the fixing device 1, the aligning device 10 with the reference star 11 fixed to it and the fixing system 1, 6 can be made rotationally secure.

The present invention thus enables a rotationally secured fixing device to be relatively simply inserted into, for example, a bone, by using for example only two parts: the fixing device and at least one securing element. This reduces the manufacturing costs of such a fixing system. Furthermore, cleaning such a fixing system is relatively simple, due to the use of, for example, only two parts.

FIG. 4 shows a fixing system in accordance with an alternative aspect of the present invention.

To fix a positioning element, such as for example the reference star 11 shown in FIG. 3, to an element, such as for example a bone, Kirschner wires or Schanz screws 20*a*, 20*b*, known in their own right, can also be used and inserted into a bone in the known way. The distance D between them can for example be 0.1 to 100 mm, preferably 0.1 to 10 mm. A fixing device is guided or attached along the Kirschner wires or Schanz screws 20*a*, 20*b* which comprises through-bores 23*a*, 23*b* for the wires or screws 20*a*, 20*b*. The fixing device 21 can be fixed rotationally securely to the wires or screws 20*a*,20*b* by means of one or more arresting elements 22, which can for example be shifted in order to produce a frictional connection with one or more Kirschner wires or Schanz screws. If the fixing device 21 is positioned by activating an arresting element 22, then protruding wires or screws can be cut off and a positioning element can be arranged on the fixing device 21, inserted into a recess 21*a* and fixed by means of, for example, suitable screws.

The fixing device 21 can be arranged fixed in place and rotationally secure on an element, such as for example a bone, via two elements inserted into a bone at the distance D from each other, such as for example Kirschner wires or Schanz screws.

What is claimed is:

1. A fixing device for a medical instrument, comprising:
   an operative section including an insertable portion configured for insertion into a bone, wherein the operative section is provided with a thread, the insertable portion of the operative section having a longitudinal axis and including at least one guide for at least one securing element, said guide being at least one of a bore or recess formed in said operative section,
   wherein said guide opens axially toward an outer axial end of the operative section to allow axial insertion of the securing element into the guide, and a longitudinal centerline of said guide is offset from a longitudinal centerline of said insertable portion of the operative section,
   wherein when the securing element is inserted longitudinally into and moved axially along the guide, a longitudinally extending portion of the securing element cooperatively engages the bone and the operative section to preclude rotation of the operative section relative to the bone; and
   a positioning element coupled to the operative section, said positioning element being trackable in a surgical navigation system.

2. A fixing device as set forth in claim 1, wherein said fixing device comprises a shaft and a head, said shaft including said operative section.

3. A fixing device as set forth in claim 2, wherein said shaft further comprises an intermediate section between the operative section and said head.

4. A fixing device as set forth in claim 3, wherein said intermediate section and said operative section have respective diameters, and the diameter of said intermediate section is larger than the diameter of said operative section.

5. A fixing device as set forth in claim 3, wherein said at least one guide includes a first part in the operative section, and a second part in the intermediate section.

6. A fixing device as set forth in claim 1, wherein said operative section is at least one of formed as a nail or formed with edges running approximately parallel to the direction of insertion into the object.

7. A fixing device as set forth in claim 1, wherein said operative section is tapered at its lower end.

8. A fixing system comprising a fixing device as set forth in claim 1 and at least one securing element configured for guidance by the guide.

9. A fixing system as set forth in claim 8, wherein said securing element comprises a threaded section.

10. A fixing system as set forth in claim 8, wherein said guide and said securing element are formed in such a way that said securing element, when inserted into said guide, exhibits substantially no play in relation to the guide.

11. A fixing system as set forth in claim 8, wherein said at least one securing element comprises a longitudinal centerline and a terminal end coaxial with the longitudinal centerline, and wherein said at least one securing element and at least one guide are configured such that when the at least one securing element is placed in the at least one guide, the longitudinal centerline of the securing element is at least parallel to the centerline of the guide, and the terminal end of the at least one securing element extends out from an outer surface of the insertable portion.

12. The fixing system as set forth in claim 8, wherein when said fixing device is inserted into the bone and the securing element is inserted into the guide, the securing element interacts with the bone to secure the fixing device to the bone.

13. A fixing device as set forth in claim 1, wherein said positioning element is a reference star.

14. The fixing device as set forth in claim 1, wherein the positioning element comprises an alignment device including a first member coupled to the operative section, a second member having a longitudinal centerline and configured to receive a trackable marker, and an adjustment device operatively coupled to the first member and the second member, wherein an angular relationship between the longitudinal centerline of the insertable portion and the longitudinal centerline of the second member is alterable via the adjustment device.

15. The fixing device as set forth in claim 14, wherein the operative section includes a connection element for coupling to the first member, said connection element including a plurality of projections and/or recesses on a surface of the connection element, and the first member comprises a plurality of projections and/or recesses on a surface of the first member, wherein the first member is couplable to the connection element in a plurality of different and fixed orientations, wherein when coupled the projections and/or recesses of the connection element engage the other of the projections and/or recesses of the first member.

16. The fixing device as set forth in claim 14, wherein the operative section includes a connection element for coupling to the first member, said connection element rotationally asymmetrical.

17. A fixing system for attaching a medical device to a bone, comprising:
   an operative section including an insertable portion configured for insertion into the bone, said insertable portion of the operative section having a longitudinal axis, wherein the operative section is externally threaded for screwing into the bone;
   an axially extending groove formed in the operative section, said groove extending parallel to the longitudinal axis of the operative section, wherein a longitudinal centerline of the groove is offset from a longitudinal centerline of the operative section; and a removable securing element for axial insertion along the groove after the operative section has been inserted in the bone, wherein when at least a portion of the securing element is axially inserted in the groove, a longitudinal extending portion of the securing element extends outwardly from the operative section and interacts with the bone to fixedly retain the securing element in the bone, and the removable securing element interacts with the groove to prevent rotation of the operative section relative to the bone; and a positioning element coupled to the operative section, said positioning element being trackable in a surgical navigation system.

18. A fixing system as set forth in claim 17, wherein the securing element has an externally threaded portion that interacts with the groove.

19. A fixing system as set forth in claim 17, wherein the operative section has external threads, and the groove intersects the threads.

* * * * *

UNITED STATES PATENT AND TRADEMARK OFFICE
CERTIFICATE OF CORRECTION

PATENT NO. : 7,862,568 B2  
APPLICATION NO. : 11/681385  
DATED : January 4, 2011  
INVENTOR(S) : Stefan Vilsmeier et al.

It is certified that error appears in the above-identified patent and that said Letters Patent is hereby corrected as shown below:

Front Page the following should appear:
        (30) Foreign Application Priority Data
        August 3, 2001 (EP) 01 118 708.5

Signed and Sealed this
Twentieth Day of March, 2012

David J. Kappos
*Director of the United States Patent and Trademark Office*